United States Patent [19]

Peacock, III et al.

[11] Patent Number: 5,549,551
[45] Date of Patent: Aug. 27, 1996

[54] ADJUSTABLE LENGTH BALLOON CATHETER

[75] Inventors: James C. Peacock, III, Saratoga; Gregory M. Hyde, Sunnyvale; Wilfred J. Samson, Saratoga, all of Calif.; Michael Clayman, Carmel, Ind.

[73] Assignee: Advanced Cardiovascular Systems, Inc., Santa Clara, Calif.

[21] Appl. No.: 361,825

[22] Filed: Dec. 22, 1994

[51] Int. Cl.⁶ .................................................. A61M 29/00
[52] U.S. Cl. ............................ 604/96; 606/194; 604/102
[58] Field of Search ........................... 604/96, 101, 102, 604/264, 280; 606/192, 194

[56] References Cited

U.S. PATENT DOCUMENTS

| | | | |
|---|---|---|---|
| 4,564,014 | 1/1986 | Fogarty et al. | 606/194 |
| 4,763,654 | 8/1988 | Jang | 604/101 X |
| 5,019,042 | 5/1991 | Sahota | 604/101 |
| 5,092,839 | 3/1992 | Kipperman | 604/53 |
| 5,246,421 | 9/1993 | Saab | 604/96 |
| 5,304,132 | 4/1994 | Jang | 604/96 |
| 5,380,283 | 1/1995 | Johnson | 604/96 |
| 5,415,635 | 5/1995 | Bagaoisan et al. | 604/96 |

*Primary Examiner*—Corrine M. McDermott
*Attorney, Agent, or Firm*—Crosby, Heafey, Roach & May

[57] ABSTRACT

A dilatation catheter having a balloon with an inflated length than can be adjusted according to the length of stenosis to be dilated. In one embodiment an exterior sheath having an expandable distal tip is employed about a elongated balloon which can be longitudinally adjusted so as to expose a length of balloon which provides a working balloon length required to dilate the stenosis. In another embodiment, the balloon has independently inflatable chambers. In yet another embodiment, the balloon has longitudinal tubular sections which expand sequentially higher pressures. Other means are also described.

12 Claims, 5 Drawing Sheets

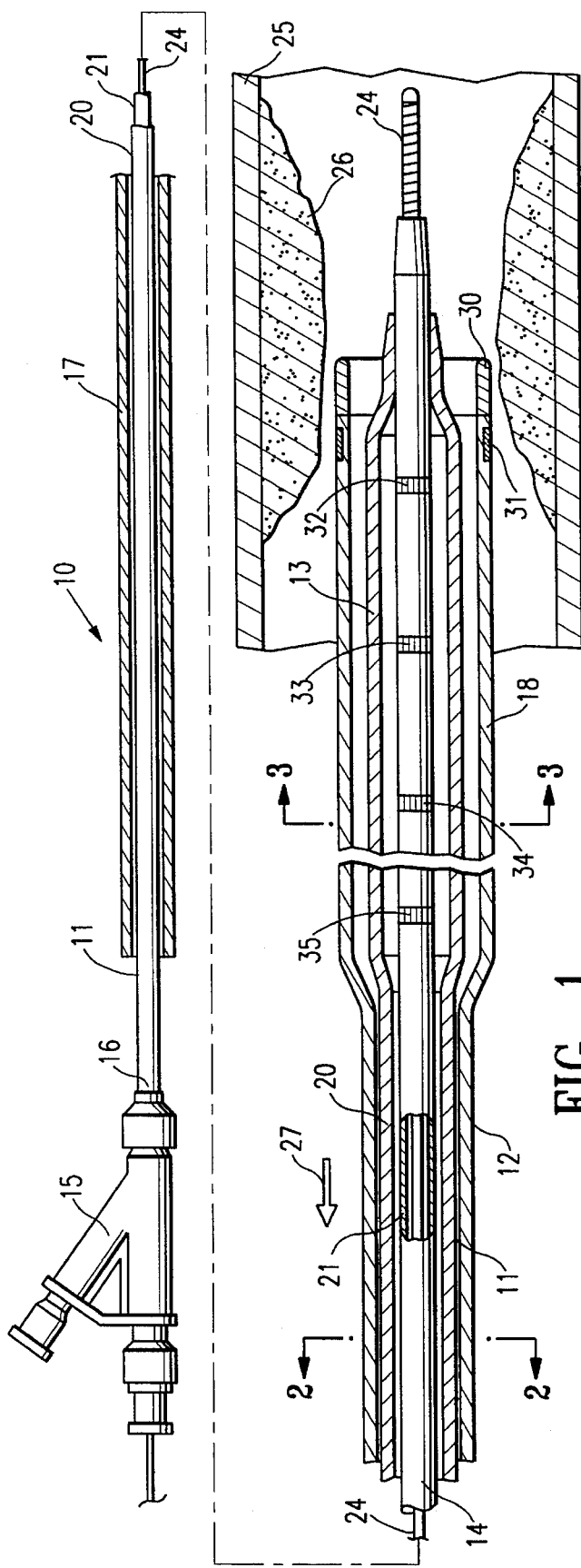
FIG. 1
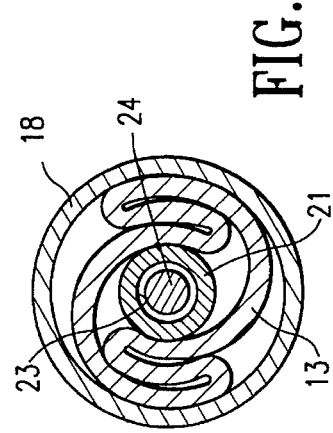
FIG. 2
FIG. 3

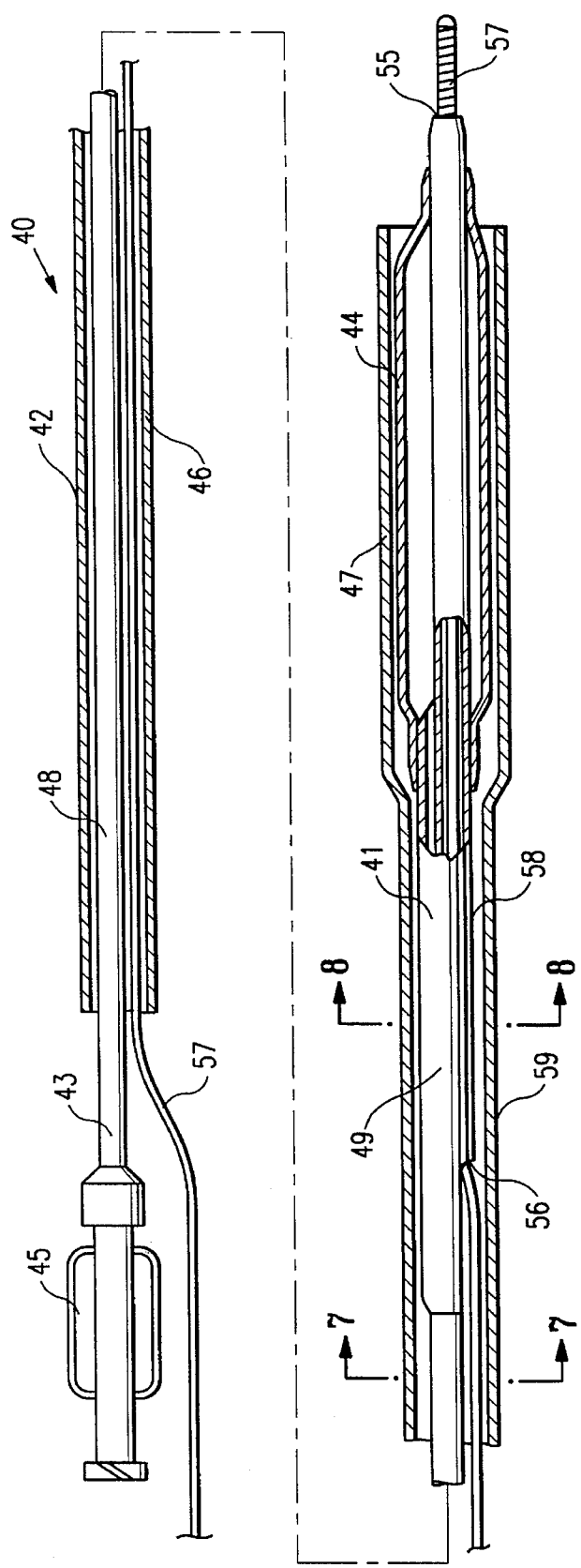
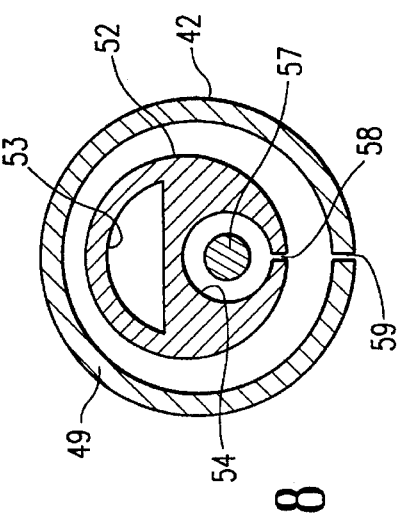
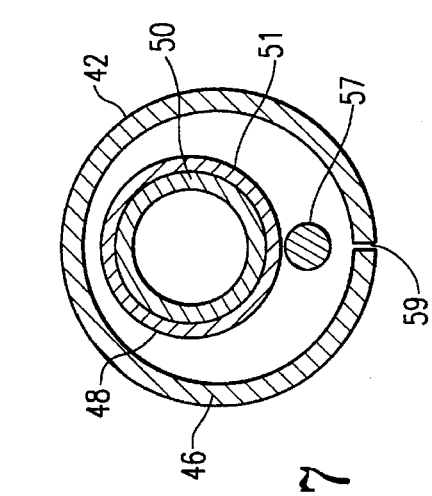
FIG. 6
FIG. 7
FIG. 8

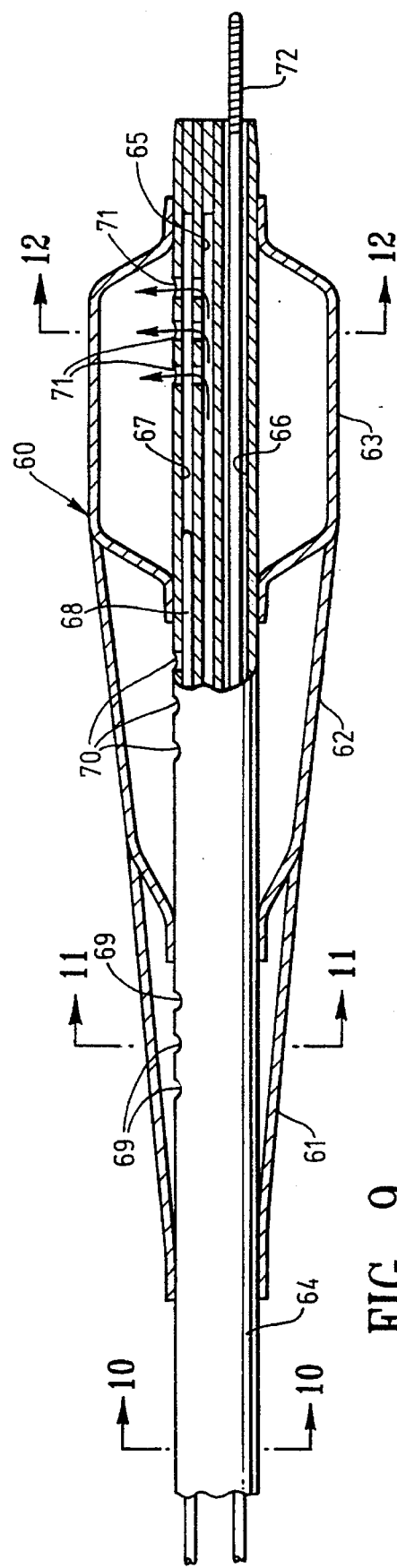
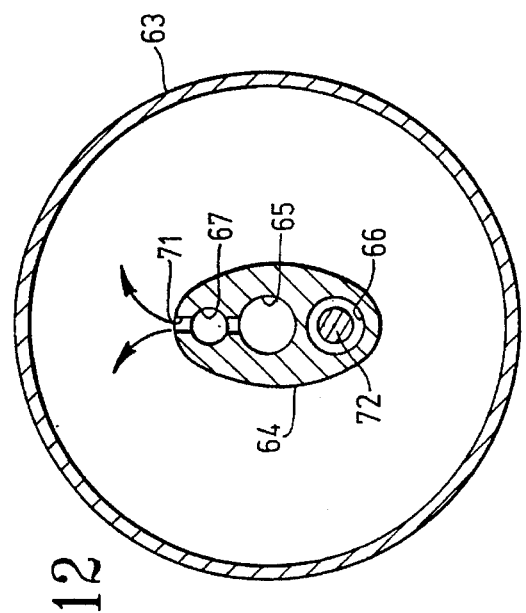
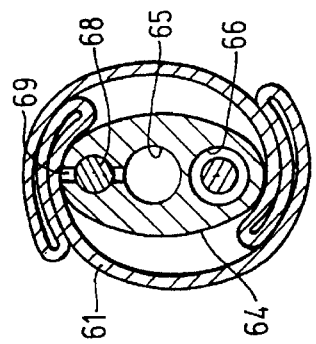
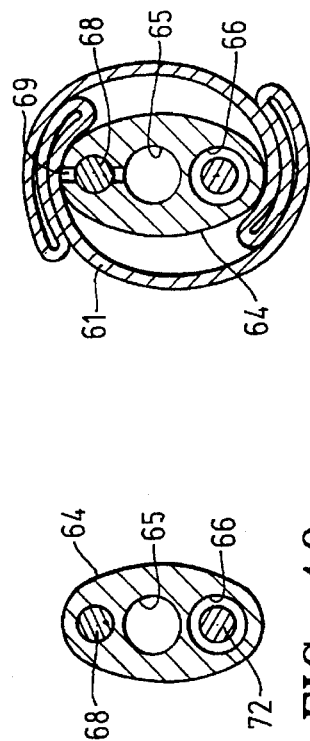
FIG. 9
FIG. 12
FIG. 11
FIG. 10

ADJUSTABLE LENGTH BALLOON CATHETER

FIELD OF THE INVENTION

This invention generally relates to balloon dilatation catheters which are used in procedures such as percutaneous transluminal coronary angioplasty (PTCA) procedures.

BACKGROUND OF THE INVENTION

In typical PTCA procedures, a guiding catheter having a preshaped distal tip is percutaneously introduced by a Seldinger technique into the vascular system of a patient and advanced within the system until the preshaped distal tip of the guiding catheter is disposed within the ascending aorta adjacent the ostium of the desired coronary artery. The guiding catheter is relatively stiff because it has to be twisted or torqued from its proximal end, which extends outside the patient, to turn the distal tip of the guiding catheter so that it can be guided into the desired coronary ostium. A balloon dilatation catheter is introduced into and advanced through the guiding catheter and out its distal tip into the patient's coronary artery until the balloon on the distal extremity of the dilatation catheter is properly positioned across the lesion to be dilated. Once properly positioned, the balloon is inflated one or more times to a predetermined size with radiopaque liquid at relatively high pressures (e.g., generally 4–12 or more atmospheres) to dilate the stenotic region of the diseased artery. When the dilatations have been completed, the balloon is finally deflated so that the dilatation catheter can be removed from the dilated stenosis to allow the resumption of normal blood flow through the dilated artery.

There are several types of balloon dilatation catheters which are now widely available, including over-the-wire catheters, fixed-wire catheters, rapid exchange type catheters (which are a type of over-the-wire catheter) and perfusion type catheters (which may be either over-the-wire or fixed-wire catheters).

Commercially available dilatation catheters have balloons with lengths ranging from about 20 to about 40 mm to handle stenosis of various lengths. However, many times the length of the balloon chosen for an angioplasty procedure is inappropriate. For example, when multiple stenosis are to be dilated, the length of one stenosis may be of significantly different length than another requiring a balloon of different length. This necessitates using multiple catheters increasing the cost and complexity of the intravascular procedure. Additionally, dilatation catheters having a range of suitable balloon lengths must be stocked and made available to the physician. What has been needed and heretofore unavailable is a dilatation catheter with a balloon which can effectively dilate stenotic regions having a variety of lengths. The present invention satisfies this and other needs as will be described hereinafter.

SUMMARY OF THE INVENTION

The present invention is directed to a dilatation catheter assembly which provides a dilatation balloon with a variable working length to accommodate a wide variety of stenotic lengths.

The dilatation catheter assembly of the present has a catheter shaft with proximal and distal ends, an inner inflation lumen extending within the catheter shaft from the proximal end of the shaft to a location spaced proximally from the distal end of the shaft, an inflatable dilatation member on the distal portion of the catheter shaft having an interior in fluid communication with the inner inflation lumen to facilitate inflation of the inflatable dilatation member and means to control which portion of the inflatable dilatation member expands upon the direction of inflation fluid thereto.

In one presently preferred embodiment the catheter assembly has an outer sheath with an inner lumen extending along the length thereof and with a distal extremity configured to envelop the inflatable dilatation member in a deflated condition, which may have a larger profile than the proximal shaft. Preferably, the inner lumen of the distal extremity of the sheath has a larger internal diameter than the inner lumen of the proximal portion of the sheath in order to facilitate receiving the inflatable dilatation member in a deflated condition. The length of the distal extremity of the sheath which receives the dilatation member should be at least one half, preferably as long as the length of the working surface of the dilatation member. The sheath/dilatation catheter assembly is configured so that the sheath and the dilatation catheter are longitudinally moveable with respect to each other. The distal end of the sheath is provided with a greater degree of expandability so that when the balloon is inflated the distal end of the sheath expands so as to shape the proximal taper of the balloon.

This catheter assembly is used essentially the same as a dilatation catheter, with the assembly being advanced through a guiding catheter which has its distal end seated within the ostium of the desired coronary artery and out the end of the guiding catheter into the patient's coronary artery. The sheath may be moved proximally with respect to the catheter to expose the desired length of the balloon before or after the balloon is positioned within the stenotic region. For example, for the first dilatation the balloon length is chosen to be the same size or slightly larger than the stenosis to be dilated. There is a common belief that fewer dissections occur when the working length of the balloon is longer than the stenotic region to be dilated so that when the balloon is inflated the end thereof can expand against healthy portions of the patient's artery. The expansion of the balloon in this manner is essentially radial stress and relatively little or no longitudinal stress which can create dissections. Subsequent dilatations of the same stenosis may require much higher pressure in a portion which was not completely dilated because it was much harder than other portions of the stenosis. Rather than subject the entire stenotic region to the higher pressure, the working length of the balloon may be shortened so that only the portion of the stenosis which had been incompletely dilated will be redilated.

The sheath supports the catheter and provides for improved pushability of the catheter, particularly with long balloons which have poor push transmission due to the long thin walled balloon region of the distal shaft. An additional advantage of the sheath is that after a first dilation the balloon can be pulled back into the distal portion to regroom the balloon so that wings which form when a vacuum is pulled on the interior of the balloon are wrapped about the inner tubular member extending through the interior of the balloon rather than extend out laterally. This regrooming reduces the effective profile of the balloon.

In another preferred embodiment of the invention the catheter assembly has an elongated inflatable balloon member with a plurality of independently inflatable balloon sections with means to inflate the balloon sections to provide a desired balloon length. In this embodiment the catheter shaft has an inflation lumen and a guidewire lumen as in the previous embodiment and a third inner lumen which has an obturator slidably disposed therein and which is adapted to block the passage of inflation fluid to the interior of balloon sections through passageways provided in fluid communication with the balloon sections. In use, the obturator is withdrawn proximally within the third inner lumen to allow inflation fluid to flow from the inflation lumen to the interior of one or more of the balloon sections to provide a desired balloon length.

In yet another embodiment of the invention the balloon is provided with a plurality of inflatable sections which are formed of material which expands at different pressures, e.g. at sequentially higher pressures, so that the sections can be inflated to a preselected pressure to inflate the desired number of inflatable balloon sections. The material from which the balloon sections are formed may be different compositions or of the same composition but with different processing to provide the expansions at different pressures. An example of the latter balloons is disclosed in copending application Ser. No. 07/917,812, filed Jul. 21, 1992, which is incorporated herein in its entirety. See also copending applications Ser. No. 07/758,630, filed Sep. 12, 1991, Ser. No. 07/918,232, filed Jul. 23, 1992, and Ser. No. 08/179,752, filed on Jan. 6, 1994, which is a continuation of the above application Ser. No. 07/758,630. These applications are incorporated herein in their entirety.

Other means for controlling which portion of the balloon expands upon direction of inflation fluid thereto is to provide heating means to raise the temperature of the balloon portion which is to be expanded so the heated portion of the balloon preferentially expands.

The catheter of the invention provides a single catheter which can be used to dilate stenoses of a wide range of lengths by merely adjusting the working length of the balloon. These and other advantages of the invention will become more apparent from the following detailed description of the invention when taken in conjunction with the accompanying exemplary drawings.

BRIEF DESCRIPTION OF THE DRAWINGS

FIG. 1 is an elevational view, partially in section, of an dilatation catheter assembly embodying features of the invention.

FIG. 2 is a transverse cross-sectional view of the catheter assembly shown in FIG. 1 taken along the lines 2—2.

FIG. 3 is a transverse cross-sectional view of the catheter assembly shown in FIG. 1 taken along the lines 3—3.

FIG. 6 is an elevational view, partially in section, of an alternative embodiment of the invention.

FIG. 7 is a transverse cross-sectional view of the embodiment shown in FIG. 6 taken along the lines 7—7.

FIG. 8 is a transverse cross-sectional view of the embodiment shown in FIG. 6 taken along the lines 8—8.

FIG. 9 is a partial, elevational view of another embodiment.

FIG. 10 is a transverse cross-sectional view taken along the lines 10—10 shown in FIG. 9.

FIG. 11 is a transverse cross-sectional view taken along the lines 11—11 shown in FIG. 9.

FIG. 12 is a transverse cross-sectional view taken along the lines 12—12 shown in FIG. 9.

DETAILED DESCRIPTION OF THE INVENTION

Figure 4:
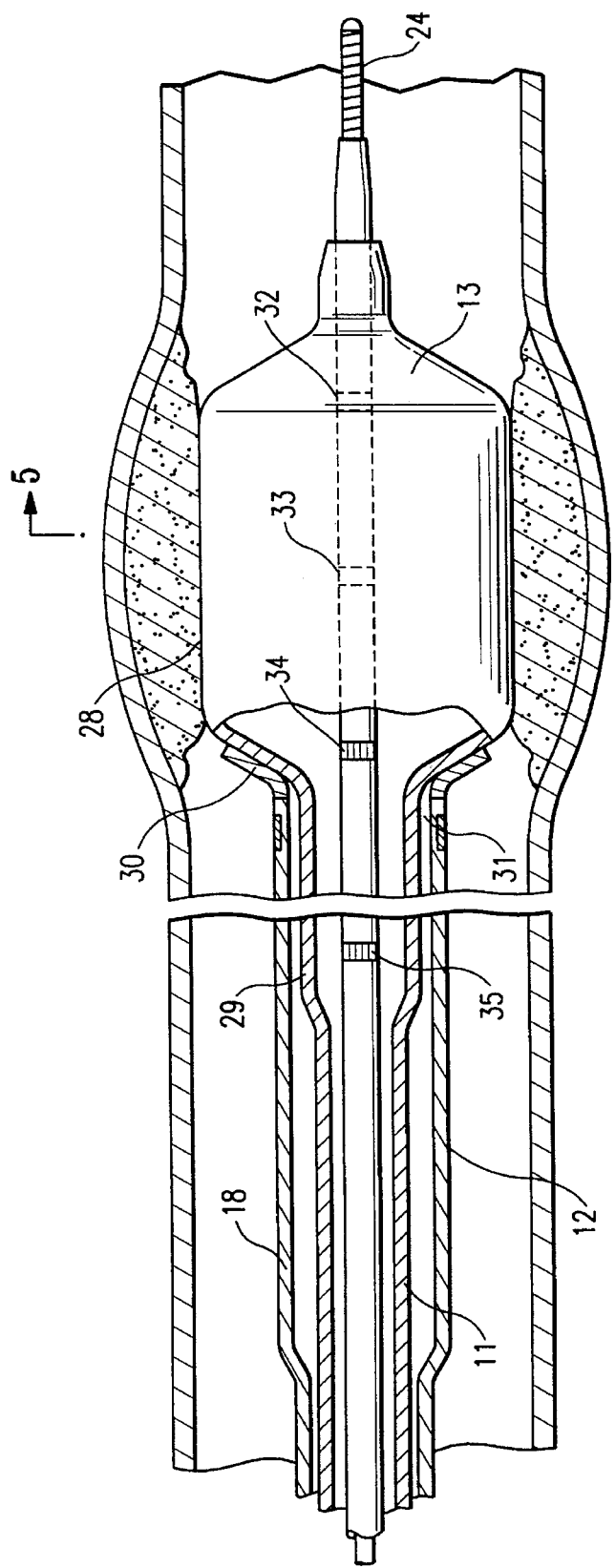
FIG. 4 is a partial elevational view of the assembly shown in FIG. 1 with the sheath partially removed from the inflatable member and the exposed portion of the inflation member being inflated.
Figure 5:
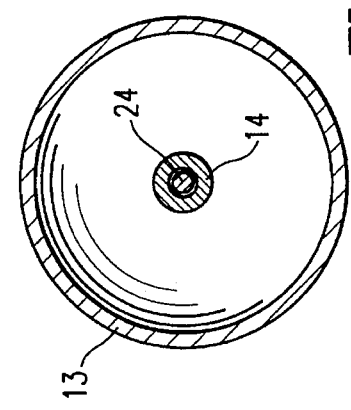
FIG. 5 is a transverse cross-sectional view of the catheter assembly shown in FIG. 4 taken along the lines 5—5.

FIGS. 1–5 illustrate a catheter assembly 10 embodying features of the invention. The catheter assembly 10 includes a balloon dilatation catheter 11 and an outer sheath 12. The balloon dilatation catheter 11 comprises an inflatable balloon 13, an elongated catheter shaft 14 and an adapter 15 mounted on the proximal end 16 of the elongated catheter shaft. The outer sheath 12 includes an elongated shaft 17 disposed about and slidable over the catheter 11 and an expanded distal portion 18 which is adapted to receive the inflatable balloon 13. To maintain the expanded distal portion 18 of the sheath 12 as small as possible, the interior of the balloon 13 is preferably subjected to a vacuum to form as small a profile as possible as shown in FIG. 3.

The catheter shaft 14 of the embodiment shown in FIGS. 1–5 is of a concentric design, comprising an outer tubular member 20 and an inner tubular member 21 disposed within the outer tubular member and defining with the outer tubular member an annular lumen 22 which is configured to direct inflation fluid to the interior of the balloon 13. The inner tubular member 21 is provided with an inner lumen 23 which is configured to slidably receive a guidewire 24. If desired, the catheter shaft 14 may be of dual lumen design such as depicted in the distal section of the embodiment shown in FIGS. 6–8 to be described hereinafter.

The sheath 12 is slidably disposed about the dilatation catheter 11 so that when the catheter assembly 10 is advanced into the patient's artery 25 to dilate a stenosis 26, the sheath can be moved in the direction indicated by arrow 27 shown in FIG. 1 to at least partially uncover the balloon 13 so that, when inflation fluid is introduced into the interior of the balloon 13, the uncovered portion of the balloon will expand to dilate the stenosis as shown in FIG. 4. In this manner the effective working length 28 of the balloon 13 can be adjusted to accommodate stenoses of various lengths. The expanded distal portion 18 of the sheath 12 is sufficiently inelastic to retain the remaining portion 29 of the balloon 13 within the sheath portion 18 and to prevent the significant inflation thereof. Upon the completion of the dilatation, the balloon 13 is deflated and may be pulled completely back into the expanded distal portion 18 of the sheath 12 so that both the dilatation catheter 11 and the sheath 12 of the assembly 10 can be removed together or advanced together to another site for stenotic dilatation. Alternatively, the sheath 12 and the dilatation catheter can be moved independently.

As shown in FIGS. 1 and 4 the sheath 12 has an elastically expandable distal tip 30 which conforms to and, to a certain extent, shapes the proximal end of the inflated portion of balloon 13 when the balloon is inflated. When the balloon 13 is deflated, the expanded distal tip 30 will elastically recoil to essentially its pre-expanded size. A radiopaque marker 31 is provided on the distal end of sheath 12 to the expandable distal tip 30 which allows the physician to determine fluoroscopically its location within a patient. Radiopaque markers 32, 33, 34 and 35 are provided on the inner tubular member 21 to allow the physician to determine the relative position of the distal end of the sheath 12 with respect to balloon 13, i.e. how much of the balloon extends out of the sheath. The expandable distal tip 30 may have radiopaque material incorporated therein, e.g. barium salt, in lieu of marker 31.

The working length of the balloon is generally at least about 2 cm, preferably about 4 to about 20 cm. The inflated diameter of the balloon may range from about 0.5 to about 10 mm, preferably about 1 to about 4 mm, The catheter shaft, the balloon and the sheath can be formed from conventional materials such as melt processable thermoplastic polymers, e.g. polyethylene, polyethylene terephthalate, polyester-polyamide such as Hytrel® and an ionomer such as Surlyn® which are available from the E. I. DuPont, deNemours & Company. The sheath can be formed in a laminate construction, e.g. where one layer of the laminate is a relatively high strength to withstand the balloon inflation pressure without significant expanding, e.g. polyethylene terephthalate or a high density polyethylene and the another layer is a relatively low strength but more flexible to provide good flexibility for tracking, e.g. a polyester-polyamide such as Hytrel®, a low density polyethylene or a suitable polyurethane. Braided or wound supporting strand may be incorporated into the wall of the catheter shaft to provide, in whole or in part, resistance to expansion while maintaining flexibility.

Reference is made to FIGS. 6–8 which depict an embodiment of the invention with rapid exchange features. The catheter assembly 40 includes a rapid exchange type dilatation catheter 41 and an outer sheath 42. The dilatation catheter 41 includes a catheter shaft 43, a dilatation balloon 44 and an adapter 45. The sheath 42 includes a proximal shaft portion 46 and an expanded distal shaft portion 47 which is configured to receive a deflated balloon 44. The sheath 42 is provided with an expandable distal tip as in the prior embodiment. The catheter shaft 43 includes a proximal portion 48 and a distal portion 49. The proximal portion 48 comprises a hypotube 50 of stainless steel or a pseudoelastic NiTi alloy provided with an outer plastic jacket or covering 51. The distal section 49 is of dual lumen design and includes an inflation lumen 53 and a guidewire receiving lumen 54 which extends between the distal guidewire port 55 in the distal end of the catheter and a proximal guidewire port 56 which is proximal to the balloon 44 and spaced a short distance (e.g. about 5 to about 50 cm) from the distal end of the catheter. A guidewire 57 is disposed within lumen 54. A slit 58 may be provided in the distal section 49 to facilitate removal of guidewire 57 from the catheter shaft. A slot 59 may also be provided in the proximal portion 46 of the sheath 42 for the same reason and to allow longitudinal movement of the sheath relative to the rapid exchange dilatation catheter. The distal shaft section is formed of melt processable thermoplastic polymer material such as polyethylene or a polyester-polyamide such as Hytrel®. If desired, the proximal shaft portion 46 of the sheath 42 may be provided with a proximal guidewire port (not shown) to facilitate the rapid exchange of the sheath at a location proximal to the guidewire port 56. The proximal shaft portion 46 may also be provided with a longitudinal groove on the same side of the shaft as the proximal guidewire port which is configured to receive a guidewire extending out of the proximal guidewire port to reduce the profile of the entire assembly proximal to the proximal guidewire port.

FIGS. 9–12 depict an alternative embodiment of the invention wherein balloon 60 with separately inflatable balloon sections 61, 62 and 63 are provided which are mounted on a distal portion of catheter shaft 64. The catheter shaft 64, which is shown in more detail in FIGS. 10–12, has an inflation lumen 65, a guidewire receiving inner lumen 66 and a third inner lumen 67 which has an obturator 68 slidably disposed therein. Longitudinal displacement of the obturator 68 within the third inner lumen 67 is utilized to block the passageways to the ports 69, 70 and 71 which are in fluid communication with the respective interiors of balloon sections 61–63 and thereby control which balloon sections are inflated. FIG. 9 depicts the most distal balloon section 63 inflated. The obturator 68 in this instance is disposed within the third inner lumen 67 so as to block the passageways 69 and 70 leading to the interior of balloon sections 61 and 62, as shown in FIG. 11, but not to block the passageways 71 leading to the interior of balloon section 63, as shown in FIG. 12. If a longer balloon is desired, the obturator 68 can be moved proximally within the third inner lumen 66 a sufficient distance so that the passageways 70 leading to the interior of balloon section 62 are no longer blocked and inflation fluid will pass therethrough to the interior of the balloon section 62 and inflate this balloon section. The last balloon section may be inflated in essentially the same manner if an even longer balloon is desired. A guidewire 72 is slidably disposed within the inner lumen 66.

Figure 13:
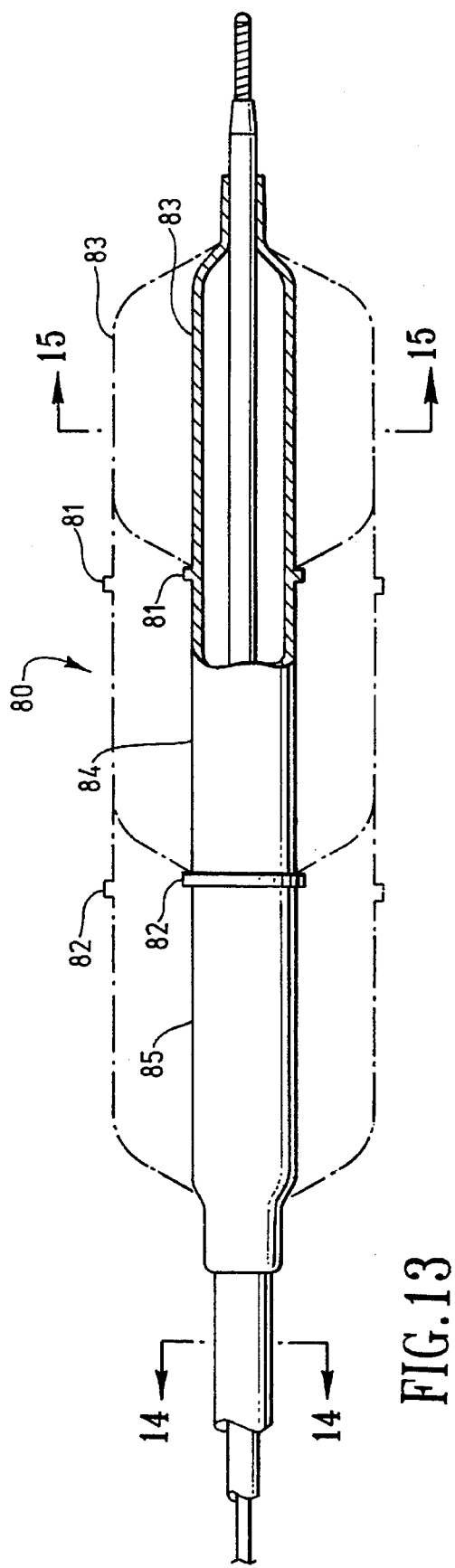
FIG. 13 is a partial elevational view a another embodiment of the invention.
Figure 15:
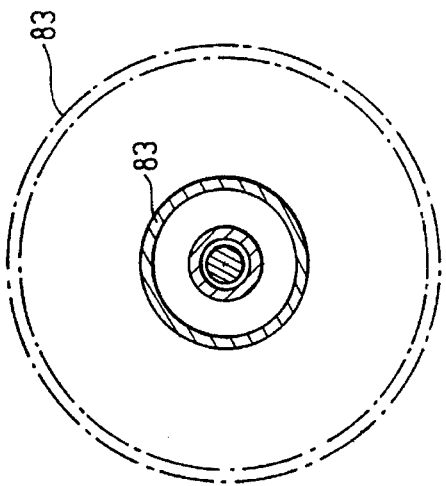
FIG. 15 is a transverse cross-section view of the embodiment shown in FIG. 13 taken along the lines 15—15.
Figure 14:
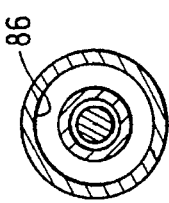
FIG. 14 is a transverse cross-section view of the embodiment shown in FIG. 13 taken along the lines 14—14.

FIGS. 13–15 depict another alternative embodiment of the invention wherein an elongated balloon 80 is provided with one or more ribs 81 and 82 which separate the balloon into three sequentially inflatable balloon sections 83, 84 and 85. The ribs 81 and 82 restrict the expansion of the balloon sections under sequentially higher pressures. For example, upon directing inflation fluid through inflation lumen 86, the first balloon section 83 is first inflated upon reaching the desired inflation pressure. The pressure of the inflation fluid must be increased to a second level higher than the first pressure to cause the first rib 81 to expand in order to inflate the second balloon section 84. The pressure of the inflation fluid must be increased to a third, even higher, pressure level to expand the second rib 82 in order to inflate the third balloon section 85. The balloon sections in their inflated conditions are shown in phantom. The ribs may be on the exterior of the balloon 80 as shown or on the interior thereof. They may be separate from or integral with the balloon 80.

Similar expansions of the balloon sections can be effected by providing balloon sections of differing wall thicknesses so that the balloon section with the thinnest wall inflates at the lowest pressure, the balloon section with the thickest wall inflates at the highest pressure and one or more balloon sections having intermediate wall thicknesses inflating at intermediate level pressures.

Other means for providing a plurality of balloon sections which expand an different pressures is to form the balloon of suitable polymer material which allows variations in the heat treatments or other steps in the manufacturing of the balloon sections to adjust the inflation pressure for the balloon sections. A suitable material is a olefinic ionomer sold under the trademark Surlyn® which has been heat treated in the manner described in copending application Ser. No. 07/917, 812 which has been incorporated herein. Briefly, these procedures may include heat treating the balloon sections at different temperatures and/or irradiating the balloon sections at different levels of radiation. A catheter with this balloon structure would be used in essentially the same manner as the previously discussed alternative embodiments.

The invention has been described herein in terms of certain preferred embodiments. It will be readily apparent to those skilled in the art that various modifications and improvements may be made to the invention. For example, elements of one embodiment may be used with another embodiment, such as the concentric shaft design shown in FIGS. 6–8 may be used in the embodiment shown in FIGS. 1–5 in lieu of the dual lumen design. Other modification can be made without departing from the scope of the depending claims.

What is claimed is:

1. A balloon dilatation catheter assembly comprising:
    a) a balloon dilatation catheter having
        an elongated catheter shaft which has proximal and distal ends and an inner inflation lumen extending therein to a location spaced proximally from the distal end of the catheter shaft;
        an inflatable balloon which has proximal and distal ends, a length and a desired inflated diameter, which is disposed on a distal portion of the elongated catheter shaft about the location spaced proximally from the distal end of the catheter shaft and which has an interior in fluid communication with the inner inflation lumen; and
    b) a longitudinally moveable sheath, which has an inner lumen with smaller transverse dimensions than a desired inflated diameter of the inflatable balloon, which has a relatively inexpandable distal extremity disposed about at least a portion of the inflatable balloon spaced proximally of the distal end of the inflatable balloon so that upon the introduction of inflation fluid within the interior of the inflatable balloon only a portion of the inflatable balloon not covered by the inexpandable distal extremity of the sheath expands to a desired inflated diameter, and which has an expandable distal tip distal to the inexpandable distal extremity and much shorter than the length of the balloon which expands upon the inflation of the balloon to shape a portion of the balloon distally adjacent to the expandable distal tip.

2. The balloon dilatation catheter assembly of claim 1 including a distal guidewire port provided in the distal end of the catheter, shaft a proximal guidewire port spaced proximally from the distal end of the catheter shaft, and distally from the proximal end of the catheter shaft and a guidewire receiving lumen extending between the proximal and distal ports.

3. The balloon dilatation catheter assembly of claim 2 wherein the proximal guidewire port is spaced about 5 to about 50 cm from the distal end of the catheter shaft.

4. The balloon dilatation catheter assembly of claim 2 including a first tubular member which defines at least in part the guidewire receiving lumen.

5. The balloon dilatation catheter assembly of claim 1 wherein the sheath has a proximal and a distal portion and the inner lumen which extends within the distal portion of the sheath is provided with larger internal transverse dimensions than the inner lumen of the proximal portion thereof to facilitate receiving the inflatable balloon.

6. A balloon dilatation catheter assembly comprising:
    a) an elongated catheter shaft having proximal and distal ends, an inner inflation lumen extending therein to a location spaced proximally from the distal end of the catheter shaft, and a guidewire receiving inner lumen extending to a port in the distal end of the catheter shaft; and
    b) an elongated inflatable balloon which is disposed on a distal portion of the elongated catheter shaft about the location spaced proximally from the distal end, of the catheter shaft which has at least two longitudinally disposed tubular sections which have a means on an exterior portion therebetween to restrict the radial expansion thereof so that the most distal of the tubular section inflates at a first internal pressure and the other tubular section inflates at a second internal pressure higher than the first internal pressure.

7. The balloon dilatation catheter assembly of claim 6 wherein the elongated inflatable balloon is at least about 2 cm in length.

8. The balloon dilatation catheter assembly of claim 6 wherein the elongated inflatable balloon is about 4 to about 20 cm in length.

9. The balloon dilatation catheter of claim 6 wherein the means on the exterior between the two tubular sections of the elongated inflatable balloon to restrict the expansion thereof is a rib extending circumferentially about the balloon.

10. The balloon dilatation catheter assembly of claim 6 wherein the a least two longitudinally disposed tubular sections expand at sequentially higher pressures from the most distal to the most proximal tubular sections.

11. A balloon dilatation catheter assembly comprising:
    a) an elongated catheter shaft having proximal and distal ends, an inner inflation lumen extending therein to a location spaced proximally from the distal end of the catheter shaft, a port in the distal end of the catheter shaft, and a guidewire receiving inner lumen extending to the port in the distal end of the catheter shaft;
    b) an inflatable balloon which has a plurality of independently inflatable interior chambers, and which is disposed on a distal portion of the elongate catheter shaft about the location spaced proximally from the distal end;
    c) a third inner lumen extending within the shaft to the most distal of the plurality of independently inflatable chambers;
    d) a plurality of passageways for inflation fluid which are in fluid communication with the inner inflation lumen and an independently inflatable interior chamber and which pass through the third inner lumen; and
    e) an obturator which is disposed and longitudinally movable within the third inner lumen and which has a distal extremity dimensioned to occlude one or more inflation passageways to prevent inflation fluid from passing from the inflation lumen to the interior of an independently inflatable chamber.

12. A method of performing an angioplasty procedure, comprising:
    a) providing a balloon dilatation catheter assembly which includes:
        an elongated catheter shaft having proximal and distal ends, an inner inflation lumen extending therein to a location spaced proximally from the distal end of the catheter shaft, a port in the distal end of the catheter shaft, and a guidewire receiving inner lumen extending to the port in the distal end of the catheter shaft;
        an inflatable balloon which has a plurality of independently inflatable interior chambers, and which is disposed on a distal portion of the elongated catheter shaft about the location spaced proximally from the distal end;
        a third inner lumen extending within the shaft to a location which is disposed within the most distal of the plurality of independently inflatable chambers;

a plurality of inflation passageways for inflation fluid which are in fluid communication with the inner inflation lumen and an independently inflatable interior chamber which pass through the third inner lumen; and an obturator which is disposed and longitudinally movable within the third inner lumen and which is dimensioned on its distal extremity to occlude one or more inflation passageways to prevent inflation fluid from passing from the inflation lumen to the interior of an independently inflatable chamber;

b) advancing the balloon dilatation catheter through a patient's vasculature until the inflatable balloon thereon is disposed within a stenotic region to be dilated; and c) adjusting the location of the obturator disposed within the third inner lumen to occlude at least one inflation passageway to prevent inflation fluid from passing from the inflation lumen to the interior of an independently inflatable chamber; and d) inflating at least one inflatable chamber to dilate the stenosis.

* * * * *